United States Patent [19]

Hashimoto et al.

[11] 4,337,082
[45] Jun. 29, 1982

[54] HERBICIDAL COMPOSITION COMPRISING TRIAZINONE COMPOUND

[75] Inventors: Shunichi Hashimoto, Sonehigashi; Hiromichi Oshio, Osaka; Masato Mizutani, Kyoto; Yuzuru Sanemitsu, Hyogo; Haruhiko Katoh, Hyogo; Seizo Sumida, Hyogo, all of Japan

[73] Assignee: Sumitomo Chemical Company, Limited, Osaka, Japan

[21] Appl. No.: 233,178

[22] Filed: Feb. 10, 1981

[30] Foreign Application Priority Data

Feb. 13, 1980 [JP] Japan .................................. 55/17043
Feb. 19, 1980 [JP] Japan .................................. 55/19914
Feb. 19, 1980 [JP] Japan .................................. 55/19915

[51] Int. Cl.³ .................... C07D 253/06; A01N 43/64
[52] U.S. Cl. ......................................... 71/93; 544/182
[58] Field of Search ........................... 71/93; 544/182

[56] References Cited

U.S. PATENT DOCUMENTS 3,824,229 7/1974 Szekeres et al. .................... 544/182

FOREIGN PATENT DOCUMENTS 288889 2/1953 Switzerland ........................ 544/182
828988 2/1960 United Kingdom ................ 544/182

OTHER PUBLICATIONS

Szekeres et al., *J. Org. Chem.*, vol. 38, pp. 3277-3281 (1973).

Primary Examiner—John M. Ford
Attorney, Agent, or Firm—Birch, Stewart, Kolasch & Birch

[57] ABSTRACT

A herbicidal composition which comprises as an active ingredient a herbicidally effective amount of a triazinone compound of the formula:

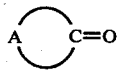

wherein A is $-NH-N=CHCH_2NH-$, $-NH-NHCH_2CH_2NH-$ or $-NH-N=CHC(NHOH)=N-$, and an inert carrier.

9 Claims, No Drawings

HERBICIDAL COMPOSITION COMPRISING TRIAZINONE COMPOUND

The present invention relates to a herbicidal composition comprising a triazinone compound.

The triazinone compounds representable by the formula:

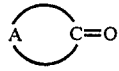  (I)

wherein A is —NH—N=CHCH$_2$NH—, —NH—NHCH$_2$CH$_2$NH— or —NH—N=CHC(NHOH)=N—, have been found to exhibit a herbicidal activity against Gramineae grasses such as barnyard grass (*Echinochloa crus-galli*), large crabgrass (*Digitaria sanguinalis*), green foxtail (*Setaria viridis*), water foxtail (*Alopecurus geniculatus*), annual bluegrass (*Poa annua*) and wild oat (*Avena fatua*) as well as broad-leaved weeds such as redroot pigweed (*Amaranthus retroflexus*), common lambsquarters (*Chenopodium album*), common chickweed (*Stellaria media*), smartweed (*Polygonum scabrum*), catchweed bedstraw (*Galium aparine*), black nightshade (*Solanum nigrum*), annual morningglory (*Ipomoea purpurea*) and jimsonweed (*Datura stramonium*).

Advantageously, the triazinone compounds (I) produce a strong herbicidal potency upon application to farmland by soil treatment prior to the germination of grasses and weeds or foliar treatment at the growth period of grasses and weeds without causing any harmful effect on various crop plants (e.g. rice plant, wheat, corn, cotton, soybean, sugarbeet, peanut, sunflower) and vegetables (e.g. lettuce, tomato). In the soil treatment, a distinct herbicidal activity of the triazinone compounds (I) is seen even against the grasses and weeds of large seeds such as annual morningglory, catchweed bedstraw and wild oat. It is characteristic that a strong herbicidal activity is produced against Gramineae weeds such as wild oat by foliar treatment. It is also characteristic that a residual effect is exerted over a long period of time. In addition, the triazinone compounds (I) may be applied to the paddy field so as to prevent and exterminate the paddy field annual and perennial grasses and weeds such as barnyard grass, pickerel weed (*Monochoria vaginalis*), tooth cup (*Lotara indica*), *Dopatrium junceum*, slender spikerush (*Eleocharis aciculalis*) and hardstem bulrush (*Scirpus serotinus*) without any phytotoxicity to rice plants.

Accordingly, the triazinone compounds (I) are useful as herbicides applicable for paddy field and farmland. They are also useful as herbicides to be employed for orchard, lawn, pasture, tea garden, mulberry field, rubber plantation, forest, non-agricultural land, etc. applications.

The triazinone compounds (I) are intended to mean the following three compounds:

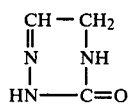  (Ia)

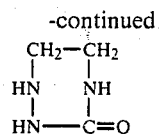  (Ib)

and

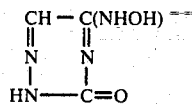  (Ic)

Among them, the compound (Ia), i.e. 3-oxo-2,3,4,5-tetrahydro-1,2,4-triazine, is per se known [J. Org. Chem., 38, 3277 (1973)]. However, its herbicidal activity has never been reported in any literature. The compound (Ib), i.e. 3-oxo-hexahydro-1,2,4-triazine, and the compound (Ic), i.e. 5-hydroxyamino-3-oxo-2,3-dihydro-1,2,4-triazine, are per se novel, and their herbicidal activity has never been reported.

The compound (Ia) can be prepared by catalytic hydrogenation of a compound of the formula:

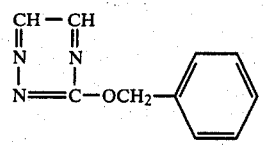  (II)

As the catalyst, there may be used any conventional catalyst for hydrogenation, and a typical example thereof is palladium-carbon. The catalytic hydrogenation is usually effected in an inert solvent such as dimethylformamide, ether, tetrahydrofuran or dioxane.

The compound (Ib) can be prepared by catalytic hydrogenation of a compound of either one of the formulas:

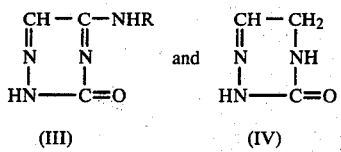

(III)  (IV)

wherein R is hydrogen, hydroxyl, amino, lower alkylamino or phenylamino. Examples of the catalyst are platinum oxide, palladium, etc. The catalytic hydrogenation is usually carried out in an inert solvent (e.g. water, methanol, ethanol) at a temperature of 0° to 50° C. under a pressure of 1 to 5 atm for 1 to 12 hours.

The compound (Ic) can be prepared by reacting a compound of the formula:

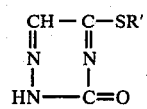  (V)

wherein R' is lower alkyl or benzyl with hydroxylamine. Hydroxylamine is usually available in a salt form (e.g. hydrochloride, sulfate) and may be used together with a base for neutralization of the acid portion forming the salt. Examples of such base are an alkali metal hydroxide (e.g. sodium hydroxide, potassium hydroxide), an alkali metal alkoxide (e.g. sodium methoxide, sodium ethoxide, potassium t-butoxide) or an alkali metal carbonate (e.g. sodium carbonate). The amount of hydroxylamine to be used may be equimolar or slightly excessive with respect to the compound (V). The reaction is usually effected in an inert solvent (e.g. methanol, ethanol, propanol, ethylene glycol, dimethylsulfoxide, dimethylformamide, dimethylcellosolve) at a temperature of 30° to 150° C. (preferably from 50° to 100° C.) for a period of 30 minutes to 20 hours.

Some typical examples of the production of the triazinone compounds (I) are set forth below.

EXAMPLE 1

3-Benzyloxy-1,2,4-triazine (1.5 g) and 10% palladium-carbon (300 mg) were added to dimethylformamide (80 ml), and the resultant mixture was subjected to catalytic hydrogenation at room temperature under a pressure of 1 atm for 4 hours. The reaction mixture was filtered, and the filtrate was concentrated to give a white solid, which was crystallized from ethanol to give 3-oxo-2,3,4,5-tetrahydro-1,2,4-triazine (Ia) (0.63 g) as white crystals. Yield, 79.7%. M.P., 122° to 125° C.

EXAMPLE 2

5-Hydroxyamino-3-oxo-2,3-dihydro-1,2,4-triazine (1.00 g) and platinum oxide (200 mg) were added to water (200 ml), and the resultant mixture was stirred at room temperature in a hydrogen atmosphere for 4 hours. The reaction mixture was filtered, and the filtrate was concentrated under reduced pressure to give a white solid, which was recrystallized from 90% aqueous ethanol to give 3-oxo-hexahydro-1,2,4-triazine (Ib) (670 mg) as white crystals. Yield, 85.8%. M.P., 194.8° C.

EXAMPLE 3

3-Oxo-2,3,4,5-tetrahydro-1,2,4-triazine (1.00 g) and platinum oxide (100 mg) were added to water (50 ml), and the resultant mixture was stirred at room temperature in a hydrogen atmosphere for 3 hours. The reaction mixture was filtered, and the filtrate was concentrated under reduced pressure to give a white solid (1.01 g). Yield, 99.0%. The solid was identified as 3-oxo-hexahydro-1,2,4-triazine (Ib).

EXAMPLE 4

Metallic sodium (0.55 g) was dissolved in methanol (40 ml) to prepare a methanolic solution of sodium methoxide. 5-Methylthio-2,3-dihydro-1,2,4-triazin-3-one (2.86 g) and hydroxylamine hydrochloride (1.67 g) were added thereto, and the resultant mixture was heated with reflux for 7 hours. After cooling to room temperature, the reaction mixture was concentrated under reduced pressure. The concentrated residue was recrystallized from 30% aqueous ethanol to give 5-hydroxyamino-3-oxo-2,3-dihydro-1,2,4-triazine (Ic) (2.32 g) as pale yellow crystals. Yield, 90.6%. M.P., 270° C.

EXAMPLE 5

To a solution of potassium hydroxide (2.02 g) in a mixture of ethanol (50 ml) and water (10 ml), 5-benzylthio-2,3-dihydro-1,2,4-triazin-3-one (6.58 g) and hydroxylamine sulfate (2.95 g) were added, and the resultant mixture was refluxed for 5 hours. The reaction mixture was cooled to room temperature and concentrated under reduced pressure. The residue was recrystallized from water to give 5-hydroxyamino-3-oxo-2,3-dihydro-1,2,4-triazine (Ic) (3.34 g) as pale yellow crystals. Yield, 87.1%.

In the practical usage of the triazinone compound (I), it may be applied as such or in any preparation form such as wettable powders, emulsifiable concentrate, granules, fine granules or dusts.

For the production of said preparation forms, solid or liquid carriers or diluents may be used. As for the solid carrier or diluent, there may be mentioned mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier or diluent, there may be employed alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent usable for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethyleneoxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. But, the surface active agent is not of course limited to these compounds. If necessary, gelatin, casein, sodium alginate, starch, agar, polyvinyl alcohol or the like may be used as an auxiliary agent.

In the herbicidal composition of this invention, the content of the triazinone compound (I) may be usually from 0.1 to 80% by weight.

The triazinone compound (I) may be used together with other herbicides to improve or enhance its herbicidal activity, and in some cases, to produce a synergistic effect. As the herbicides to be mixed therewith, there may be mentioned phenoxy series herbicides such as 2,4-dichlorophenoxyacetic acid, 2-methyl-4-chlorophenoxyacetic acid and 2-methyl-4-chlorophenoxybutyric acid (including esters and salts thereof); diphenyl ether series herbicides such as 2,4-dichlorophenyl-4'-nitrophenyl ether, 2,4,6-trichlorophenyl-4'-nitrophenyl ether, 2-chloro-4-trifluoromethylphenyl-3'-ethoxy-4'-nitrophenyl ether, 2,4-dichlorophenyl-4'-nitro-3'-methoxyphenyl ether and 2,4-dichlorophenyl-3'-methoxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine and 2-methylthio-4,6-bisisopropylamino-1,3,5-triazine; urea series herbicides such as 3-(3,4-dichlorophenyl)-1,1-dimethylurea, 3-(3,4-dichlorophenyl)-1-methoxy-1-methylurea and 1-(2,2-dimethylbenzyl)-3-p-tolylurea; carbamate series herbicides such as isopropyl-N-(3-chlorophenyl)carbamate and methyl-N-(3,4-dichlorophenyl)carbamate; thiolcarbamate series herbicides such as S-(4-chlorobenzyl)-N,N-dimethylthiolcarbamate and S-ethyl-N,N-hexamethylenethiolcarbamate; acid anilide series herbicides such as 3,4-dichloropropionanilide, N-methoxy-methyl-2,6-diethyl-α-chloroacetanilide, 2-chloro-2',6'-diethyl-N-butoxymethylacetanilide, 2-chloro-2',6'-diethyl-N-(n-propoxyethyl)acetanilide and N-chloroacetyl-N-(2,6-diethylphenyl)glycine ethyl ester; uracil series herbicides such as 5-bromo-3-sec-butyl-6-methyluracil and 3-cyclohexyl-5,6-trimethyleneuracil; pyridinium chloride series herbicides such as 1,1'-dimethyl-4,4-bispyridinium chloride; phosphorus series herbicides such as N,N-bis(-phosphonomethyl)glycine, O-ethyl-O-(2-nitro-5-methylphenyl)-N-sec-butylphosphoroamidothioate, S-(2-methyl-1-piperidylcarbonylmethyl) O,O-di-n-propyldithiophosphate and S-(2-methyl-1-piperidylcarbonylmethyl) O,O-diphenyldithiophosphate; toluidine series herbicides such as α,α,α-trifluoro-2,6-dinitro-N,N-dipropyl-p-toluidine; 5-tert-butyl-3-(2,4-dichloro-5-isopropoxyphenyl)-1,3,4-oxadiazolin-2-one; 3-isopropyl-1H-2,1,3-benzothiadiazin(4)-3H-one-2,2-dioxide; α-(β-naphthoxy)propionanilide; 4-(2,4-dichlorobenzoyl)-1,3-dimethylpyrazol-5-yl-p-toluenesulfonate and the like. But, the herbicides are not limited to these examples.

The herbicide of the invention may be applied together with insecticides, nematocides, fungicides, plant growth regulators, fertilizers, etc.

When the triazinone compound (I) is used as a herbicide, it may be applied before or after germination of grasses or weeds in an amount within a wide range. The amount may be usually from about 2–200 grams per are, preferably from about 5–50 grams per are.

Practical embodiments of the herbicidal composition according to the invention are illustratively shown in the following examples wherein part(s) and % are by weight.

PREPARATION EXAMPLE 1

Twenty-five parts of the triazinone compound (Ia), (Ib) or (Ic), 2.5 parts of a dodecylbenzenesulfonate, 2.5 parts of a ligninsulfonate and 70 parts of diatomaceous earth are well mixed while being powdered to obtain a wettable powder.

PREPARATION EXAMPLE 2

Thity parts of the triazinone compound (Ia), (Ib) or (Ic), 10 parts of an emulsifier ("Sorpol SM-100" manufactured by Toho Chemical Co., Ltd.) and 60 parts of xylene are well mixed to obtain an emulsifiable concentrate.

PREPARATION EXAMPLE 3

Five parts of the triazinone compound (Ia), (Ib) or (Ic), 1 part of white carbon, 5 parts of a ligninsulfonate and 89 parts of clay are well mixed while being powdered. The mixture is then kneaded with water, granulated and dried to obtain a granule.

PREPARATION EXAMPLE 4

Three parts of the triazinone compound (Ia), (Ib) or (Ic), 1 part of isopropyl phosphate, 66 parts of clay and 30 parts of talc are well mixed while being powdered to obtain a dust.

PREPARATION EXAMPLE 5

Fourty parts of bentonite, 5 parts of a lignin-sulfonate and 55 parts of clay are well mixed while being powdered. The mixture is then well kneaded with water, granulated and dried to obtain a granule containing no active ingredient. Ninety-five parts of the thus obtained granule are then impregnated with 5 parts of the triazinone compound (Ia), (Ib) or (Ic) dissolved in methanol. Subsequent removal of methanol gives a granule.

PREPARATION EXAMPLE 6

Ninety-five parts of bentonite of 16–48 mesh is impregnated with 5 parts of the triazinone compound (Ia), (Ib) or (Ic) dissolved in methanol. Subsequent removal of methanol gives a granule.

Some test examples which show the herbicidal activity and the fungicidal activity of the triazinone compound (I) are shown in the following Examples wherein % is by weight.

TEST EXAMPLE 1

Plastic trays (35×25×10 cm) were filled with upland soil, and seeds of redroot pigweed, annual morning-glory, catchweed bedstraw, wild oat and barnyard grass as well as seeds of rice plant and wheat were sowed therein. An aqueous composition prepared by diluting a wettable powder containing the triazinone compound (I) with water was applied onto the entire surface of the soil in an amount of 5 liters per are by the aid of a small hand sprayer. After the application, the trays were allowed to stand in a greenhouse for 20 days. Then, the herbicidal activity and phytotoxicity were evaluated on the following criteria and indicated by numerals ranging from 0 to 5. The results are shown in Table 1.

TABLE 1

| Numeral | Percentage of growth inhibition (%) |
|---------|-------------------------------------|
| 0 | 0–9 |
| 1 | 10–29 |
| 2 | 30–49 |
| 3 | 50–69 |
| 4 | 70–89 |
| 5 | 90–100 |

| | | Triazinone compound | | | | | |
|---|---|---|---|---|---|---|---|
| | | (Ia) | | (Ib) | | (Ic) | |
| Amount used (g/are) | | 80 | 40 | 80 | 40 | 80 | 40 |
| Herbicidal activity | Annual morning-glory | 5 | 5 | 5 | 5 | 5 | 5 |
| | Redroot pigweed | 5 | 5 | 5 | 5 | 5 | 5 |
| | Catchweed bed-straw | 4 | 4 | 5 | 4 | 5 | 4 |
| | Wild oat | 4 | 4 | 4 | 4 | 5 | 4 |
| | Barnyard grass | 4 | 4 | 4 | 4 | 5 | 4 |
| Phyto-toxicity | Rice plant | 0 | 0 | 0 | 0 | 1 | 0 |
| | Wheat | 0 | 0 | 1 | 1 | 1 | 1 |

TEST EXAMPLE 2

Wagner's pots (1/5000 are) were each filled with upland soil, and seeds of wild oat and barnyard grass as well as seeds of rice plant and wheat were sowed therein and grown for 2 to 3 weeks in a greenhouse. A designed amount of the triazinone compound (I) was sprayed to the foliage of the test plants over the top by means of a small hand sprayer. After this foliar application, the plants were grown for an additional 3 weeks in the greenhouse. The triazinone compound (I) was formulated into an emulsifiable concentrate and dispersed in water for application at a spray volume of 5 liters per are with addition of a wetting agent. The herbicidal activity and phytotoxicity were examined on the same criteria as in Test Example 1. The results are shown in Table 2.

TABLE 2

| Amount used (g/are) | | Triazinone compound | | | | |
|---|---|---|---|---|---|---|
| | | (Ia) | | (Ib) | | (Ic) |
| | | 40 | 20 | 40 | 20 | 40 | 20 |
| Herbicidal activity | Wild oat | 5 | 4 | 5 | 4 | 5 | 5 |
| | Barnyard grass | 4 | 4 | 5 | 4 | 5 | 5 |
| Phytotoxicity | Rice plant | 0 | 0 | 0 | 0 | 0 | 0 |
| | Wheat | 0 | 0 | 1 | 0 | 1 | 0 |

What is claimed is:

1. A herbicidal composition which comprises as an active ingredient a herbicidally effective amount of a triazinone compound of the formula:

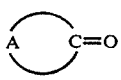 (I)

wherein A is —NH—N=CHCH₂NH—, —NH—NHCH₂CH₂NH— or —NH—N=CHC(NHOH)=N—, and an inert carrier.

2. The herbicidal composition according to claim 1, wherein the content of the active ingredient is from 0.1 to 80% by weight.

3. The herbicidal composition according to claim 1, wherein the active ingredient is the triazinone compound of the formula (I) wherein A is —NH—N=CHCH₂NH—.

4. The herbicidal composition according to claim 1, wherein the active ingredient is the triazinone compound of the formula (I) wherein A is —NH—NHCH₂CH₂NH—.

5. The herbicidal composition according to claim 1, wherein the active ingredient is the triazinone compound of the formula (I) wherein A is —NH—N=CHC(NHOH)=N—.

6. A triazinone compound of the formula:

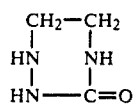 (Ib)

7. A triazinone compound of the formula:

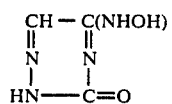 (Ic)

8. A process for preparing the triazinone compound according to claim 7, which comprises reacting a compound of the formula:

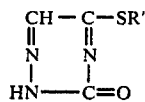

wherein R' is lower alkyl or benzyl with hydroxylamine.

9. A method for controlling the growth of weeds and/or grasses which comprises applying a herbicidally effective amount of a triazinone compound of the formula:

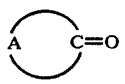 (I)

wherein A is —NH—N=CHCH₂NH—, —NH—NHCH₂CH₂NH— or —NH—N=CHC(NHOH)=N— to the area where the weeds and/or grasses grow or will grow.

* * * * *